United States Patent [19]

Falat

[11] Patent Number: 5,411,890
[45] Date of Patent: May 2, 1995

[54] METHOD FOR MEASURING ATMOSPHERIC CORROSION

[75] Inventor: Ladislav Falat, College Park, Md.

[73] Assignee: Westvaco Corporation, New York, N.Y.

[21] Appl. No.: 264,715

[22] Filed: Jun. 23, 1994

[51] Int. Cl.$^6$ ............................................. G01N 17/00
[52] U.S. Cl. ...................................... 436/6; 73/61.62; 73/104; 422/53
[58] Field of Search ...................... 73/53.01, 61.62, 86, 73/104, 785, 819, 799, 856, 859; 203/7; 269/234, 254 R; 411/75, 76, 203, 354; 422/53; 436/6

[56] References Cited

U.S. PATENT DOCUMENTS

| | | | |
|---|---|---|---|
| 2,351,644 | 6/1944 | Talley et al. | 73/51 |
| 3,014,788 | 12/1961 | Littler et al. | 422/53 X |
| 3,084,658 | 4/1963 | Schell | 116/114 |

FOREIGN PATENT DOCUMENTS

| | | | |
|---|---|---|---|
| 59-94038 | 5/1984 | Japan. | |
| 5-52723 | 3/1993 | Japan | 422/53 |

OTHER PUBLICATIONS

W. B. A., Sharp et al. *Tappi J.* 1989, 72(10), 143–145.
T. Iikawa et al. *Corr. Sci.* 1993, 35, 735–742.

*Primary Examiner*—James C. Housel
*Assistant Examiner*—Arlen Soderquist

[57] ABSTRACT

An atmospheric environmental monitoring method utilizes a corrosion test element prepared from a transparent substrate having two opposed surfaces. A corrodable film is applied to one surface of the substrate in the form of a thin wedge of metal and a security coating is applied to the opposite surface of the substrate. The surface of the corrodable film adjacent to the transparent substrate is reflective to radiation when viewed through the substrate. The security layer is designed to reflect radiation in at least the visible region of the spectrum and yet be transparent to radiation in other parts of the spectrum.

7 Claims, 1 Drawing Sheet

METHOD FOR MEASURING ATMOSPHERIC CORROSION

BACKGROUND OF INVENTION

The present invention is related to the invention disclosed in applicant's prior U.S. Pat. application Ser. No. 07/362,973, filed Jun. 8, 1989, now abandoned. It is directed to an improvement in the monitoring of atmospheric environments. More particularly, the invention relates to an improved corrosion test element and method for using the test element to determine the rate at which atmospheric corrosion takes place in a designated environment.

The present invention was developed in response to the need for a method for quickly and inexpensively measuring the rate of corrosivity of an industrial environment without requiring complex and time consuming analysis and/or manpower to obtain such results. The standard industry method currently available employs the exposure of specially prepared copper coupons. After exposure to a selected environment for a specified time period, the copper coupons are cathodically (electrochemically) reduced in an electrolyte, requiring complex glassware and instrumentation, and the time of a highly skilled technician. This method is time consuming, labor intensive and hence expensive. At least two alternate methods exist for measuring atmospheric corrosivity, one employing the measurement of the resistance of a thin pathway of copper, and the other employing vibrational frequency measurement of a copper coated quartz crystal (quartz crystal microbalance). However both of these alternatives require expensive sensors, sophisticated instrumentation, and databases relating the measured parameter change to the actual corrosion or metal disappearance rate. Obviously it would be far preferable to have available a less expensive corrosion indicator that would provide evidence of a corrosive atmosphere on a more timely basis, and which would allow the user to calculate the rate at which the corrosion is taking place.

Corrosion test elements have been used for testing the corrosion rate of metals in the presence of corrosive liquids. In U.S. Pat. No. 2,351,644, there is disclosed a test element having a quantity of the metal which is to be tested applied to a suitable carrier. The test element is placed in contact with a corrosive liquid for a designated period of time, and upon removal, the amount of the test metal removed is noted. From this test, the rate of corrosion of the metal can be calculated. In a related invention disclosed in U.S. Pat. No. 3,084,658, a moisture and corrosion indicator includes a transparent disk onto which there is applied a sensing material either as a film of cobaltous chloride or a metallic material. When exposed to moisture, the cobaltous chloride's color changes from blue to pink and then back to blue when the moisture is removed. Meanwhile, when a metallic material such as pure iron is exposed to moisture, it will rust, and the rusted surface may be seen visually when looking through the transparent disk. However, neither invention contemplates a method for determining the rate of corrosivity of an atmosphere. In the present invention, the rate of corrosivity for an environment can be determined by visually observing the rate of change in the area of the reflective surface of a corrodable metal film applied to a transparent substrate over time, as viewed through the substrate, or, when a security coating is applied to the substrate, by observing the change in reflectivity through the substrate using a suitable instrument which emits radiation in a frequency range which is not reflected by the security coating.

SUMMARY OF INVENTION

In the present invention, the corrosion test element comprises a non-corrodable, transparent substrate having a layer of corrodable metal applied to one surface of the substrate in the form of a thin wedge of the metal. In a preferred embodiment, the corrodable metal comprises a film of copper or other metallic material which may be vapor deposited or sputtered onto the surface of the substrate. In a typical construction, the test element substrate is a glass slide generally rectangular in shape, and the application of the corrodable metal is carried out so as to provide a thin wedge of the metal which ranges in thickness from about 250 Angstroms at its thinnest end to about 1,000 Angstroms at its thickest end. As prepared, both the exposed surface of the corrodable metal and the surface of the metal adjacent to the substrate, as viewed through the substrate, have the appearance of a semitransparent mirror. When the test element is placed in a corrosive environment, the corrodable metal begins to corrode. During this process, a film of corrosion products accumulates almost immediately across the entirety of the exposed surface of the corrodable metal causing this surface to lose its reflectivity. However, when the test element is viewed through the substrate, the portion of the metal that is not completely corroded remains reflective. Since corrosion takes place substantially uniformly across the entire surface of the wedge shaped metal, the thinnest end of the wedge will become completely corroded first and lose its reflectivity as viewed through the substrate. As more and more of the metal corrodes toward the thickest end of the wedge shaped metal, the amount of reflective area as viewed through the substrate will become smaller and smaller. In this regard it can be said that a reflective "front" moves across the test element towards the thickest end of the wedge shaped metal. The linear position of this "front" over time correlates with the corroded portion of the metal. Using this information, a rate of corrosivity can be calculated for the environment under observation as measured in Angstroms per year.

Although the position of the "front" for this embodiment of the invention can be determined visually, visual observation is subject to a number of inaccuracies including the fact that the substrate itself is inherently reflective. For this and other reasons it is desirable to provide a security coating on the surface of the substrate opposite from the surface having the corrodable metallic wedge. The purpose of the security coating is to mask or obscure the performance of the test element from any casual visual observation. The presence of the security layer also permits the rate of corrosivity to be measured with greater accuracy than could be accomplished by the mere visual observation of the test element. Thus, in a second embodiment of the present invention, a security coating designed to reflect radiation in at least the visible region of the electromagnetic spectrum but which is transparent to radiation in other parts of the spectrum, is applied in a substantially uniformly thick layer over the back side of the substrate. Security coatings of the type intended are generally prepared by applying multi-layers of two different metallic oxides, for example, oxides of silica, tin, indium and titanium, in one-quarter wavelength thicknesses to achieve the desired effect. For this embodiment, the reflectance of the corrodable metal wedge can be measured through the substrate using an instrument which emits radiation in the region of the spectrum where the security coating is transparent. An example of such a coating useful for the present invention may comprise layers of oxides of titanium and silica which is a visible light reflector that transmits infrared radiation. When using such a security layer, the performance of the test element can be monitored with an infrared gun or other IR emitting apparatus. If desired, one or more test elements may be placed in the environment to be monitored to yield time dependent information relative to the corrosivity of the environment.

DETAILED DESCRIPTION

Figure 1:
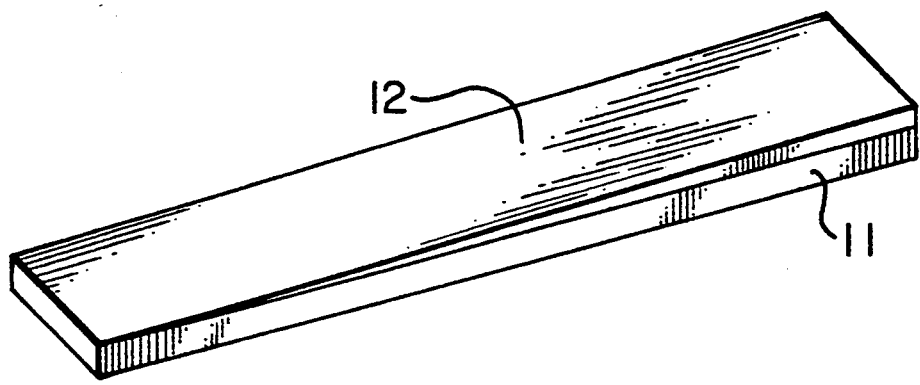
FIG. 1 is a perspective view of a corrosion test element according to a first embodiment of the present invention.
Figure 2:
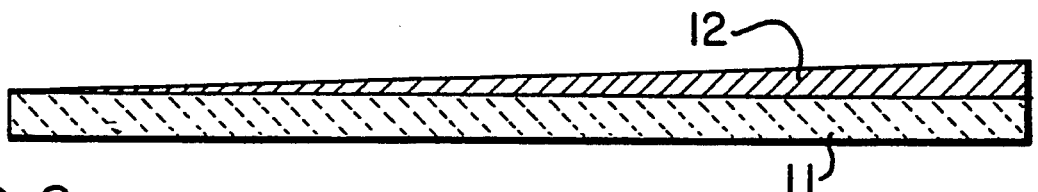
FIG. 2 is a side view of the test element of FIG. 1.

Referring now to the drawing, FIG. 1 illustrates a corrosion test element according to the present invention comprising a substrate 11 onto which there is applied a wedge-shaped layer of corrodable metal 12. The substrate 11 is preferably optically transparent, inert and non-corrodable, and may be selected from the group consisting of glass, polycarbonate, plexiglass and quartz. The corrodable metal wedge 12 is preferably copper but other metallic materials such as silver, zinc or iron, or the like may be substituted. The substrate 11 is sufficiently thick to support the metal wedge 12 which is vapor deposited or sputtered onto one surface in a substantially uniform wedge shape having a thickness at the thinnest end on the order of from about 200 to 300 Angstroms and a thickness at the thickest end on the order of from about 1000 to 1500 Angstroms. FIG. 2 illustrates the preferred shape of the corrodable metal wedge 12.

Figure 3:
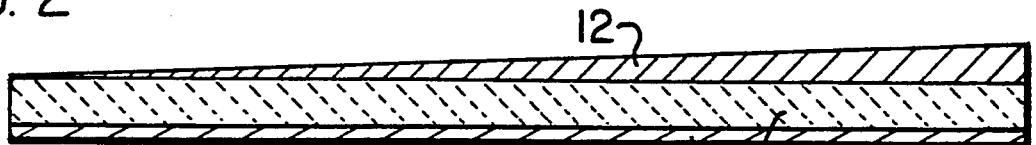
FIG. 3 is a side view of a corrosion test element according to a second embodiment of the present invention; and, FIGS. 4 and 5 are views through the substrate of the corrosion test elements of FIGS. 1-3 showing the change in position of the corrosion "front" over time.

FIG. 3 illustrates a corrosion test element in accordance with the second embodiment of the invention. For this embodiment, the back side of the substrate 11 has applied thereto a security coating 13 of substantially uniform thickness. The security coating as described hereinbefore is preferably designed to be reflective to radiant energy in the visible region of the electromagnetic spectrum, and transparent to radiation in other parts of the spectrum. In a preferred embodiment the security coating 13 is comprised of layers of the oxides of titanium and silica, which is transparent to infrared radiation. It will be understood, however, that other security coatings transparent to different radiation sources outside the visible region of the spectrum could readily be substituted for the preferred coating. Such coatings can be prepared from multi-layered stacks of other different metallic oxides.

Figure 4:
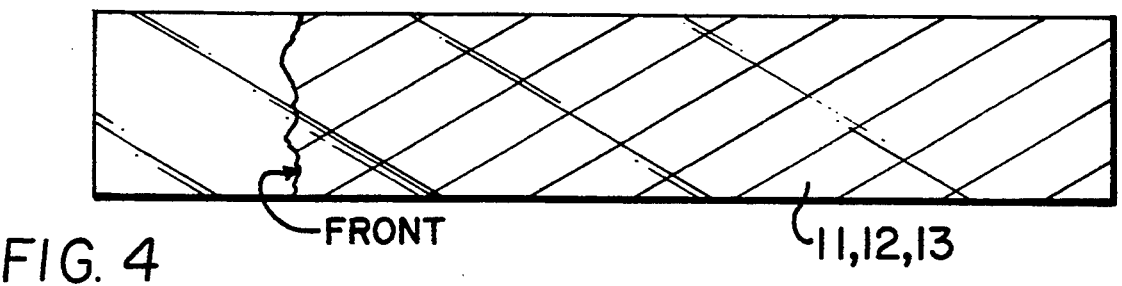
Figure 5:
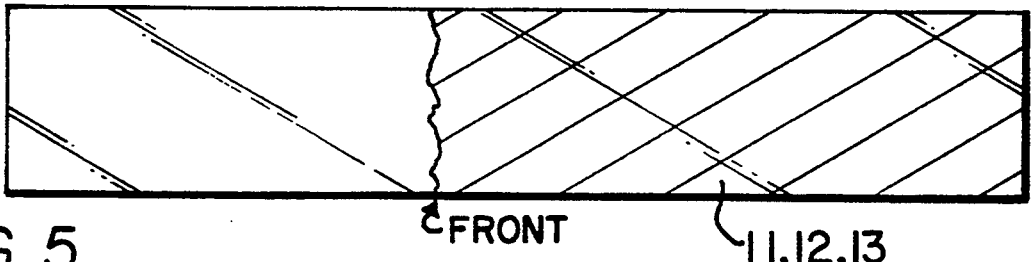

In use, one or more corrosion test elements are placed in the environment to be monitored. The exposed surface of the corrodable metal wedge 12 becomes almost immediately non-reflective, while the surface adjacent to the substrate 11 remains reflective until such time that the corrodable metal 12 begins to corrode away. During this period, the reflective surface of the metal wedge 12 can be observed through the substrate 11, or where a security coating 13 is used, monitored with a device which emits radiation that pierces the security coating, to observe the movement of the corrosion "front" as the corrodible material 12 corrodes from its thinnest end to its thickest end. A determination of the reduction in area of the reflective surface over time yields a rate of corrosivity for the monitored environment. FIGS. 4 and 5 illustrate the reflective "front" as observed over time through the substrate 11, or the substrate 11 and security coating 13, using a suitable instrument which emits radiation which pierces the security coating.

While there has been fully described herein the basic principles of the present invention, it will be understood that changes or variations in the embodiments disclosed could readily occur to those skilled in the art. Accordingly, the invention should not be so limited, except as set forth in the appended claims.

What is claimed is:

1. A corrosion test element comprising a non-corrodable, transparent substrate having two opposed surfaces, a layer of corrodable material applied to one surface of said substrate and a security coating applied to the opposite surface of said substrate, said layer of corrodable material having a thickness which varies along a length thereof and wherein the security coating is reflective to radiant energy in the visible region of the electromagnetic spectrum and transparent to radiant energy in adjacent parts of the electromagnetic spectrum.

2. The test element of claim 1 wherein the corrodable material is applied to the substrate in the form of a wedge having a thickness at the thinnest end of from about 200 to 300 Angstroms and a thickness at the thickest end of from about 1000 to 1500 Angstroms.

3. The test element of claim 2 wherein the corrodable material is a metal selected from the group consisting of iron, zinc, copper and silver.

4. The test element of claim 1 wherein the security coating comprises a multi-layered stack of two different metallic oxides selected from the group consisting of oxides of silica, tin, indium and titanium.

5. The test element of claim 4 wherein the security coating comprises a multi-layered stack of oxides of titanium and silica which is transparent to radiant energy in the infrared region of the spectrum.

6. The method of determining the rate of corrosivity of a selected atmosphere comprising:
 (a) preparing a corrosion test element having a layer of corrodable material applied to one surface of a transparent substrate having two opposed surfaces to form a reflective surface and a security coating applied to the opposite surface of said substrate, said layer of corrodable material having a thickness which varies along a length thereof and wherein the security coating is reflective to radiant energy in the visible region of the electromagnetic spectrum and transparent to radiant energy in adjacent parts of the electromagnetic spectrum;
 (b) placing the test element in the atmosphere to be tested;
 (c) observing the rate at which the reflective surface is reduced in size over time; and,
 (d) determining a corrosivity rate for the atmosphere in Angstroms per year.

7. The method of claim 6 wherein the security coating is transparent to radiation in the infrared region of the spectrum.

* * * * *